US011414636B2

(12) United States Patent
Tai et al.

(10) Patent No.: US 11,414,636 B2
(45) Date of Patent: Aug. 16, 2022

(54) SUBSTRATES FOR HIGH-DENSITY CELL GROWTH AND METABOLITE EXCHANGE

(71) Applicants: California Institute of Technology, Pasadena, CA (US); City of Hope, Duarte, CA (US)

(72) Inventors: Yu-Chong Tai, Pasadena, CA (US); Yang Liu, Pasadena, CA (US); Colin A. Cook, San Gabriel, CA (US); Yuman Fong, La Canada, CA (US); Nanhai G. Chen, San Diego, CA (US)

(73) Assignees: California Institute of Technology, Pasadena, CA (US); City of Hope, Duarte, CA (US)

(*) Notice: Subject to any disclaimer, the term of this patent is extended or adjusted under 35 U.S.C. 154(b) by 888 days.

(21) Appl. No.: 16/100,468

(22) Filed: Aug. 10, 2018

(65) Prior Publication Data

US 2019/0002813 A1  Jan. 3, 2019

Related U.S. Application Data

(62) Division of application No. 15/647,156, filed on Jul. 11, 2017, now Pat. No. 10,053,660.
(Continued)

(51) Int. Cl.
*C12M 1/04* (2006.01)
*C12M 1/12* (2006.01)
*C12M 1/00* (2006.01)

(52) U.S. Cl.
CPC ............ *C12M 23/24* (2013.01); *C12M 23/14* (2013.01); *C12M 23/20* (2013.01); *C12M 25/14* (2013.01); *C12M 29/04* (2013.01)

(58) Field of Classification Search
CPC ...... C12M 25/14; C12M 23/24; C12M 23/14; C12M 23/20; C12M 29/04
See application file for complete search history.

(56) References Cited

U.S. PATENT DOCUMENTS 3,948,732 A   4/1976  Haddad et al.
5,139,946 A   8/1992  Howell et al.
(Continued)

FOREIGN PATENT DOCUMENTS

EP        725134      8/1996
JP      62228269 A   10/1987
(Continued)

OTHER PUBLICATIONS

EP17828334.7, "Extended European Search Report", dated Jun. 25, 2020, 13 pages.
(Continued)

*Primary Examiner* — Gautam Prakash
(74) *Attorney, Agent, or Firm* — Kilpatrick Townsend & Stockton LLP

(57) ABSTRACT

A polymer or other substrate optimized for growing cells is described, which takes the form of a micro-thin bag with gas permeable sides. Sides of the bag can be held at a fixed distance from one another with a multitude of tiny micropillars or other spacers extending between them, keeping the bag at a predetermined thickness and preventing the bag from collapsing and the sides from sticking together. In other embodiments, the sides may be held apart by gas pressure alone. A 0.01 μm to 1000 μm parylene or other biocompatible coating over the bag outsides controls the permeability of the bag material and provides a bio-safe area for cell growth. An alternate configuration uses open-cell foam with skins coated with a biocompatible coating. Tubes going into multiple bags can be connected to a manifold that delivers gaseous oxygen or removes carbon dioxide and other waste
(Continued)

gases. Multiple bags can be stacked together tightly, with o-ring spacers in between, and housed within a vessel to form a high-surface area, ultra-compact cell growing system. For cells growing on the bags, liquid nutrients can be fed by way of the tube spacers, and oxygen and waste gases permeated through the bag sides and transported within the bags.

10 Claims, 15 Drawing Sheets

Related U.S. Application Data

(60) Provisional application No. 62/361,390, filed on Jul. 12, 2016.

(56) References Cited

U.S. PATENT DOCUMENTS

| | | | |
|---|---|---|---|
| 5,416,022 | A | 5/1995 | Amiot |
| 5,487,889 | A | 1/1996 | Eckert et al. |
| 5,686,304 | A | 11/1997 | Codner |
| 5,985,475 | A | 11/1999 | Reynolds et al. |
| 6,562,616 | B1 | 5/2003 | Toner et al. |
| 7,560,274 | B1 | 7/2009 | Fuller et al. |
| 9,410,113 | B2 | 8/2016 | Vilendrer et al. |
| 10,053,660 | B2 | 8/2018 | Tai et al. |
| 2009/0314696 | A1 | 12/2009 | Trentacosta et al. |
| 2011/0020922 | A1 | 1/2011 | Wuenn et al. |
| 2013/0261568 | A1 | 10/2013 | Martinson et al. |
| 2014/0065709 | A1 | 3/2014 | Martin et al. |
| 2014/0315296 | A1 | 10/2014 | Wilson |
| 2018/0016533 | A1 | 1/2018 | Tai et al. |

FOREIGN PATENT DOCUMENTS

| | | |
|---|---|---|
| JP | 10507363 A | 7/1998 |
| JP | 2004524046 A | 8/2004 |
| JP | 2005512530 A | 5/2005 |
| JP | 2011510656 A | 4/2011 |
| JP | 2013153744 A | 8/2013 |
| JP | 2014507959 A | 4/2014 |
| WO | 9613573 | 5/1996 |
| WO | 9738777 | 10/1997 |
| WO | 03052047 | 6/2003 |
| WO | 2008069902 | 6/2008 |
| WO | 2013096488 | 6/2013 |
| WO | 2018013606 | 1/2018 |

OTHER PUBLICATIONS

PCT/US2017/041590, "International Preliminary Report on Patentability", dated Jan. 24, 2019, 9 pages.
EP17828334.7, "Partial Supplementary European Search Report", dated Jan. 31, 2020, 15 pages.
U.S. Appl. No. 15/647,156, "Notice of Allowance", dated Apr. 23, 2018, 9 pages.
U.S. Appl. No. 15/647,156, "Restriction Requirement", dated Feb. 12, 2018, 6 pages.
PCT/US2017/041590, "International Search Report and Written Opinion", dated Sep. 29, 2017, 11 pages.

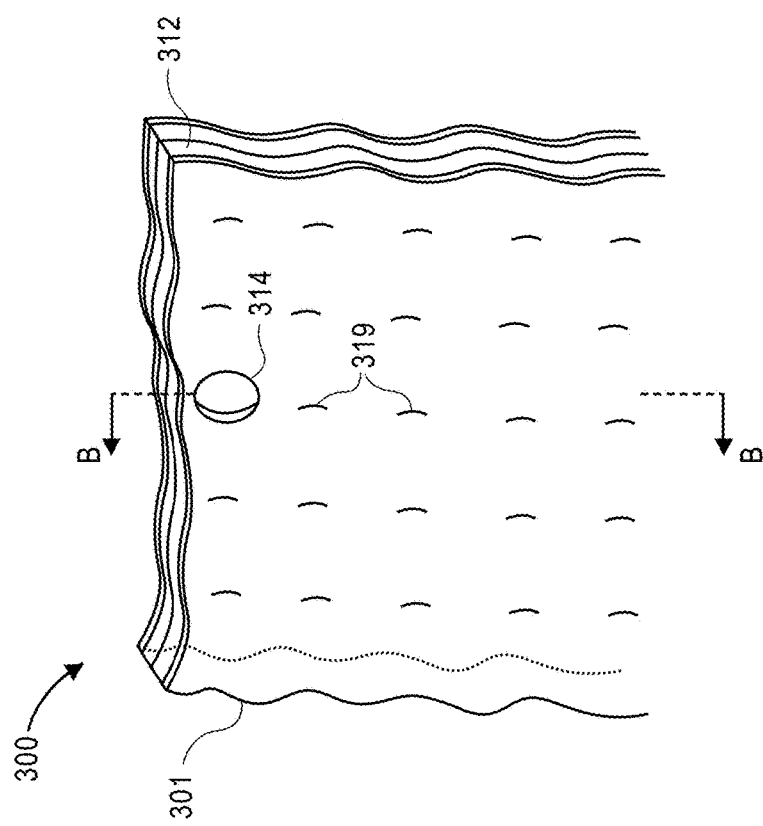
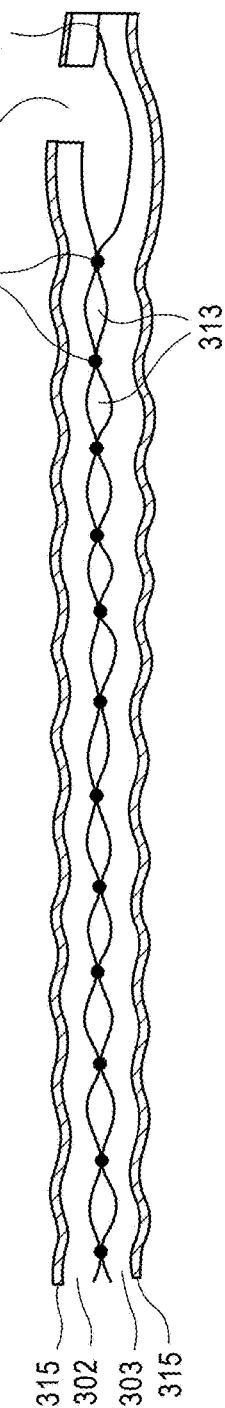
FIG. 3A
FIG. 3B

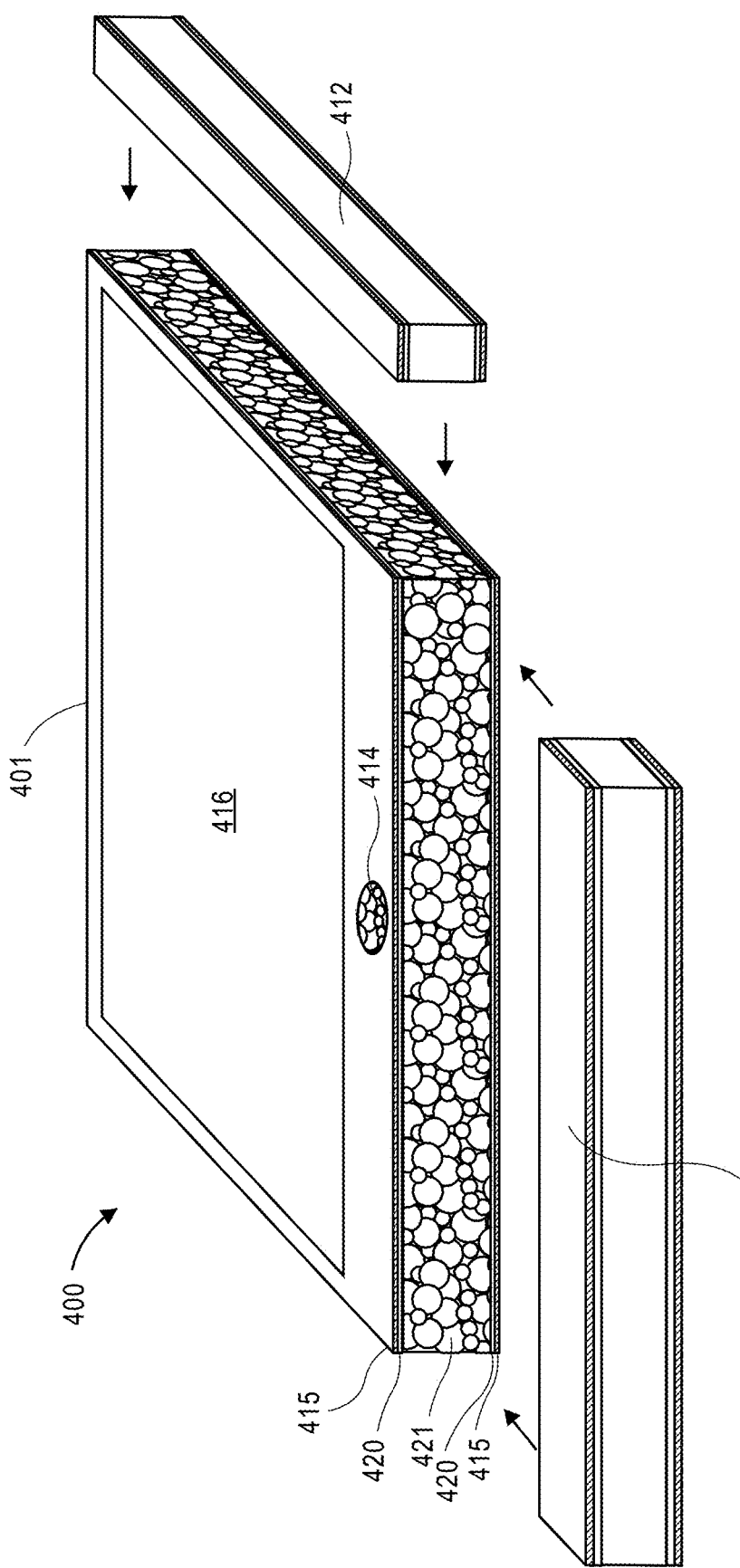

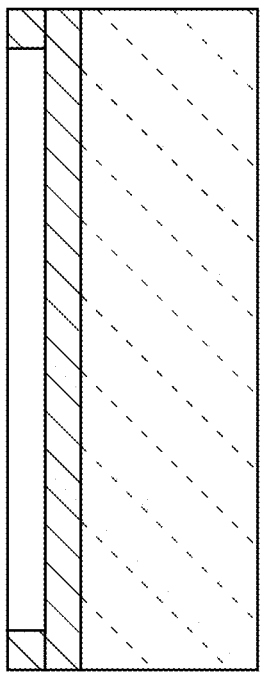
FIG. 9A
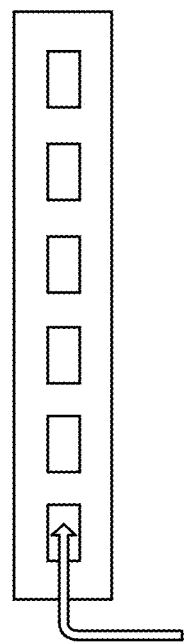
FIG. 9D
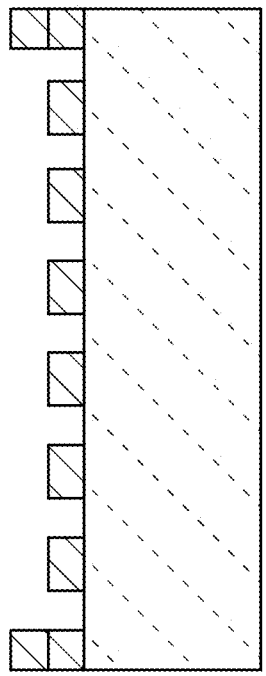
FIG. 9B
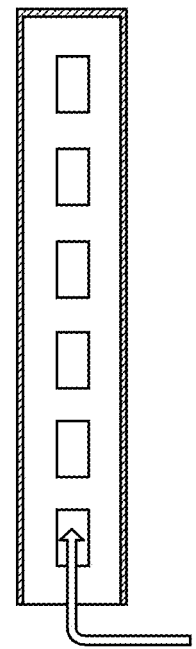
FIG. 9E
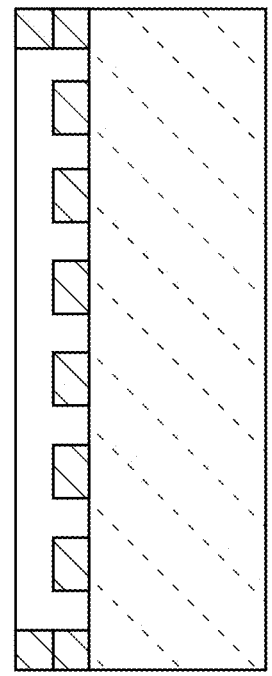
FIG. 9C
FIG. 9F

SUBSTRATES FOR HIGH-DENSITY CELL GROWTH AND METABOLITE EXCHANGE

CROSS-REFERENCES TO RELATED APPLICATIONS

This application is a divisional of U.S. application Ser. No. 15/647,156, filed Jul. 11, 2017 (U.S. Pat. No. 10,053,660, issued Aug. 21, 2018), which claims the benefit of U.S. Provisional Application No. 62/361,390, filed Jul. 12, 2016. The above applications are hereby incorporated in their entireties for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Art

Embodiments of the present invention generally relate to a bioreactor apparatus for culturing microorganisms and growing cells, including gas permeable non-collapsible and/or non-expandable bags with microfabricated features and coatings, as well as methods of manufacture and use.

2. Description of the Related Art

Large-scale high density cell culture is important for many biotechnology applications where cells are used to produce specific molecules, proteins, viruses, or other products. Increasing cell density allows for greater production per unit volume, which can help reduce costs through space savings and more concentrated product.

The challenge of high-density cell growth arises from mass transport limitations particularly with respect to oxygen, nutrients, and waste products. In low-density cell culture systems, passive diffusion of metabolites is often sufficient to meet the metabolic demands of cells; however, in high-density cell culture systems, the metabolic demand of cells exceeds supply from diffusion alone, requiring additional mass transport mechanisms such as convection.

The additional requirement of high-density cell culture is a high surface area to volume ratio, particularly for adherent cell populations. This is because many cells grow in monolayers, and their growth is inhibited once they reach confluence.

Several technologies have been developed to enhance cell density including cell factory systems, wave/stirred bioreactors with microcarriers, and perfused dialysis membrane systems.

Cell factory systems are most similar to conventional flask culture systems except that cell factory systems contain multiple layers of growth substrate within a single flask. The cell density that can be achieved is not very high due to the large spacing between layers, resulting in a low surface-to-volume ratio, and the reliance on diffusive transport for all metabolites.

Wave and stirred bioreactor systems add convection to enhance mass transport by gently mixing cell microcarriers, small neutrally buoyant particles with surface chemistry suitable for cell adhesion and growth, within a container of media. The combination of high surface area afforded by the microcarriers and the convective mixing allows for higher cell densities to be achieved compared to cell factory systems. However, convective mixing also causes shear forces on the cells, which can induce cell death, thereby limiting the degree of mixing and mass transport to cells that can be achieved. Such systems are often shear-limited due to the need to enhance mass transport through mixing rather than surface area limited.

Perfused dialysis membrane systems overcome the shear problem by perfusing gas through tightly packed semi-permeable dialysis tubes and allowing diffusion to deliver oxygen to cells. However, the geometry of the dialysis tubes prevents very high surface areas to volume ratios from being achieved. Furthermore, there are challenges with cell removal from the highly porous membranes on which the cells grow.

In summary, some challenges of high density cell growth include: 1) achieving high growth surface area to volume ratio; 2) maintaining adequate metabolite transport within the system; and 3) maintaining shear forces experienced by cells below lethal levels. While several existing technologies have attempted to overcome these challenges, there remains extensive room for improvement of the art.

BRIEF SUMMARY

Generally, very thin gas permeable plastic bags with an array of internal connection points, such as microfabricated weld points to prevent expansion and/or internal spacers to prevent collapse, are presented. The bags are coated with a thin (e.g., 2 µm and 10 µm thick) biocompatible coating, such as parylene, to control permeability and provide a surface for cells to adhere. The biocompatible coating may be subject to an oxygen plasma and/or ammonia plasma treatment, and further coatings of agarose, etc. may be applied in order to further improve cell adhesion.

Open cell foam with a skin may also be formed into an expansion resistant, collapse resistant bag. The outside skin is layered with a biocompatible coating to control permeability and provide a clean surface for cell growth, and the edged sealed to form a bag. An inlet allows air, oxygen, or other gases into the bag's interior.

In use, the bag is immersed in a nutrient-rich liquid water culture and provided with or otherwise inflated with gaseous oxygen to act as a substrate for cell growth. A cell that attaches itself to the bag is supplied with a gentle flow of gaseous oxygen through the gas permeable membrane of the bag, and it can discharge gaseous carbon dioxide or other waste gases through the bag. Meanwhile, the surrounding liquid provides nutrients to the cell and carries off its waste products.

Many such gas permeable bags may be stacked to together and their inlets connected by o-rings to form a convenient manifold. The stack can be submerged in an aquarium-like enclosure that holds the bags tightly in the stack. The o-rings, as well as beads or other spacers, serve to keep the bags separated so there is a great amount of surface area for cell growth. There is a drop off in oxygen the farther one is away from a bags, but the distance between the bags may be optimized so that a center point between two bags has sufficient oxygen for cell growth.

Some embodiments of the present invention are related to a cell-growing substrate apparatus. The apparatus includes a pair of gas permeable, polymer sheets, an array of connection points between faces of the polymer sheets, the connection points having a center-to-center spacing less-than-or-equal-to 2000 µm, a hermetically sealed edge that bonds a perimeter of the sheets together, enclosing the connection points in an interior cavity between the sheets to form an expansion resistant bag, an inlet to the bag fluidly connected with the interior cavity, and a biocompatible coating over an outside of at least one of the gas permeable sheets, the biocompatible coating having a thickness between 0.01 µm and 1000 µm.

The center-to-center spacing of the connection points can be between 100 µm and 1000 µm. The apparatus can further include an array of spacers connecting the sheets at the connection points, the spacers having a height sufficient to make the expansion resistant bag collapse resistant. A height of the spacers can be equal-to-or-greater-than one fifth the center-to-center spacing of the connection points. The spacers can be integrally formed with one of the gas permeable sheets. The apparatus can include a plurality of outside spacers abutting an outside of the expansion resistant bag. The outside spacers can be porous tubes or spheres coated with a biocompatible coating. The outside spacers can be integrally formed with one of the gas permeable sheets.

The biocompatible coating can include a parylene coating selected from the group including parylene N, parylene C, parylene D, and parylene AF-4. The thickness of the parylene coating can be between 2 µm and 10 µm. The thickness of the parylene coating can preferably be between 5 µm and 6 µm. A surface treatment area on the biocompatible coating can be configured to improve cell adhesion. The surface treatment area can be a product of an oxygen plasma-treatment, an ammonia plasma treatment, or both an oxygen plasma-treatment and an ammonia plasma treatment. A coating of agarose, collagen, lactic acid, laminin, poly-d-lysine, or poly-l-lysine can be on the surface treatment area to further enhance cell growth.

The material of the gas permeable, polymer sheets can be a polymer selected from the group including of polydimethylsiloxane (PDMS), polyethylene, and polyurethane. The gas permeable, polymer sheet can be less than 200 µm thick. An outlet from the bag can be fluidly connected with the interior cavity. A tube having a lumen fluidly connected with the inlet to or an outlet from the bag can be attached to the bag. The inlet can pass through a hole in the hermetically sealed edge of the bag. The connection points in the array can be geometrically regularly spaced apart, or irregularly spaced apart, from each other.

Some embodiments are related to a cell-growing substrate apparatus, including a sheet of polymeric open-cell foam having gas permeable skin sheets on two opposing sides, a hermetically sealed edge that bonds a perimeter of the gas permeable skin sheets together, enclosing the open-cell foam in an interior cavity between the gas permeable skin sheets to form an expansion- and collapse-resistant bag, an inlet to the bag fluidly connected with the interior cavity, and a biocompatible coating over an outside of at least one of the gas permeable skin sheets, the biocompatible coating having a thickness of 0.01 µm to 1000 µm. The sheet of polymeric open-cell foam can be 0.1 mm to 1.5 mm thick.

Some embodiments are related to a cell-growing substrate apparatus, including a watertight vessel, a stack of biocompatible material-coated, flat, expansion resistant gas permeable bags within the vessel, each bag having an associated inlet to an interior cavity of the bag, and spacers between the expansion resistant gas permeable bags.

The gas permeable bags can be stacked in vertical planes. The stack can include at least one gas permeable bag folded over onto itself. The stack can include at least one gas permeable bag coiled around itself. The apparatus can further include o-rings that space each bag apart and sealing the inlets of the bags to each other.

Some embodiments are related to a method of manufacturing a cell growing apparatus. The method includes casting a pillared gas permeable sheet having spacers on one side, the gas permeable sheet having a thickness sufficient to allow gaseous molecular oxygen to permeate therethrough yet prevent liquid water from permeating therethrough at standard room temperature and atmospheric pressure, fabricating a second gas permeable sheet, joining the second gas permeable sheet to the pillared gas permeable sheet with the spacers therebetween, hermetically sealing a perimeter of the gas permeable sheets together to form an expansion resistant bag, depositing a biocompatible coating on at least one side of the expansion resistant bag, the biocompatible coating having a thickness between 0.1 µm and 1000 µm, and treating the biocompatible coating in order to improve cell adhesion.

The pillared gas permeable sheet and second gas permeable sheet can be comprised of a polymer, and each sheet can have a thickness less than 200 µm. The method can further include forming an inlet in the expansion resistant bag and/or applying adhesive to the second gas permeable sheet.

Some embodiments are related to a method of manufacturing a cell growing apparatus. The method includes intimately contacting a pair of gas permeable, polymer sheets together, placing a heat-insulative mask having an array of through holes against the polymer sheets, the through holes having a center-to-center spacing less-than-or-equal-to 2000 µm, pressing a heated iron against the heat-insulative mask opposite the polymer sheets, a temperature of the heated iron and duration of the pressing sufficient to form an array of welds between the polymer sheets where exposed by the mask through holes, hermetically sealing a perimeter of the polymer sheets together to form a bag with an interior portion, depositing a biocompatible coating on at least one side of the bag, the biocompatible coating having a thickness between 0.1 µm and 1000 µm, and treating the biocompatible coating in order to improve cell adhesion.

The through holes can be photolithographically formed in the mask such that they are tiny. The polymer sheets can include polydimethylsiloxane (PDMS), and the heat-insulative mask includes silicone rubber.

Some embodiments are related to a method of growing and harvesting cells. The method includes providing a stack of expansion resistant, gas permeable, polymer bags, each bag having an inlet connected with a manifold, each bag having a biocompatible coating, the bags being spaced from one another by spherical beads, seeding cells into interstitial spaces between the beads and bags, flowing a liquid culture of nutrients between the interstitial spaces, pressurizing molecular oxygen gas into the expansion resistant bags through the manifold, waiting for the cells to grow, the nutrients and molecular oxygen gas supporting growth of the cells, applying trypsin to the cells to cleave their hold on the bag or beads, and flushing the cells from the beads.

The method can further include removing the bags from the beads. The method can further include infecting the cells with a virus, where the growth of the cells serves to replicate viruses, and separating the replicated viruses from the flushed cells.

BRIEF DESCRIPTION OF THE DRAWINGS

FIG. 3A is an isometric view of a gas permeable microfabricated array-welded bag in accordance with an embodiment.

FIG. 3B illustrates cross section B-B of FIG. 3A.

FIG. 4 is an isometric, exploded view of an open-cell foam gas permeable bag in accordance with an embodiment.

FIG. 9A is a cross section and illustrates a portion of a microfabricated bag manufacturing process in accordance with an embodiment.

FIG. 9B illustrates a portion of the manufacturing process of FIG. 9A.

FIG. 9C illustrates a portion of the manufacturing process of FIG. 9A.

FIG. 9D illustrates a portion of the manufacturing process of FIG. 9A.

FIG. 9E illustrates a portion of the manufacturing process of FIG. 9A.

FIG. 9F illustrates a portion of the manufacturing process of FIG. 9A.

DETAILED DESCRIPTION

Figure 1A:
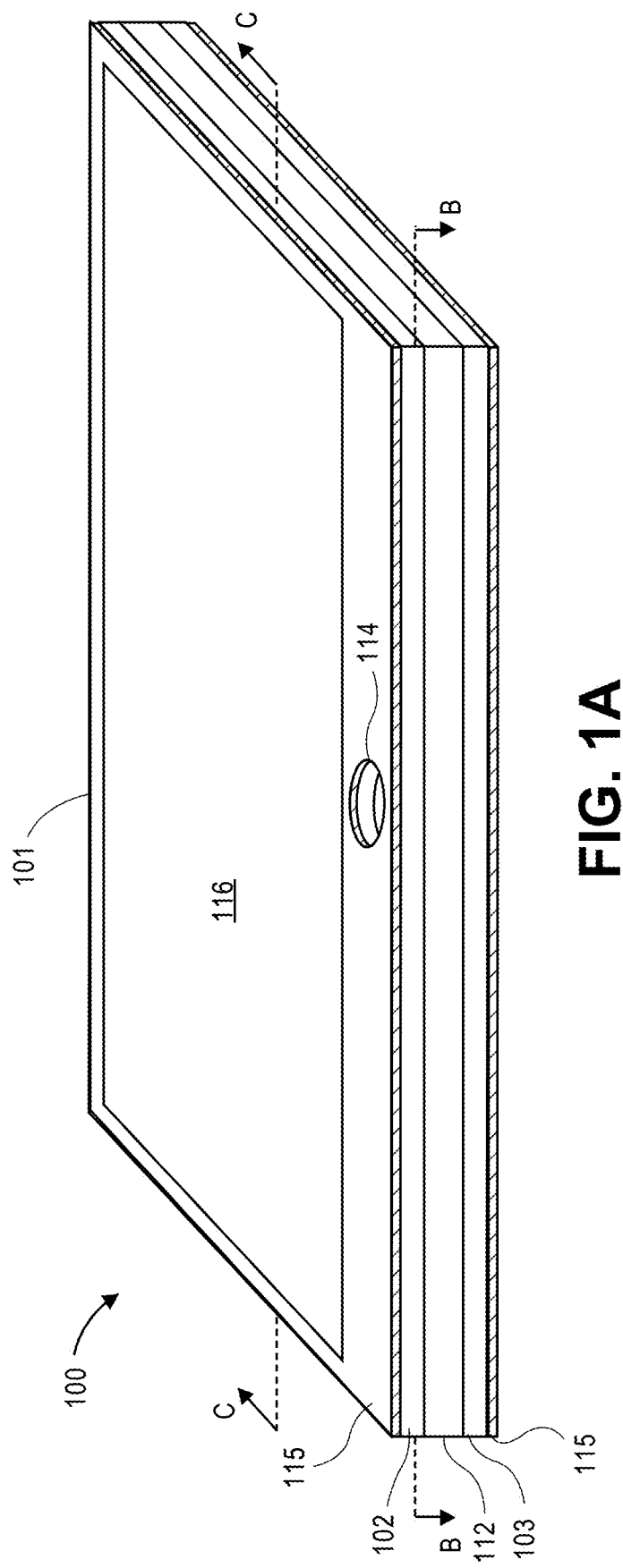
FIG. 1A is an isometric view of a gas permeable, expansion resistant, collapse resistant bag in accordance with an embodiment.

A culture system (e.g. box, container, other parts) capable of very high density cell culture is described. The inventors recognized that molecular oxygen ($O_2$) is the most limiting metabolite for cell growth due to its low solubility in cell media. By separating gas convective delivery from other nutrient delivery, it is possible to significantly increase oxygen delivery to cells without increasing detrimental shear forces.

Gas perfusable, gas permeable membrane sheets, formed into bags, provide a high surface area while delivering sufficient oxygen and gas exchange for high-density cell growth. These bags can be folded or stacked to achieve high surface area to volume ratios. Cells can be grown directly on the surface of the membranes or on substrates sandwiched between the membranes.

While the use of separate membranes for oxygen delivery is useful, there are other aspects including delivery and removal of other nutrients, solutions, cells, and viruses. For example, a gap between stacked membranes can be perfused with solutions to deliver or remove components into or out of the membrane stacks. The gap and rate of perfusion can be chosen so as to maintain suitable shear rates within the device. In another example, a network of tubes or channels can be employed throughout the system for delivery separate from the gas supply. The tubes or channels may contain pores to allow various sized particles ranging from molecules to cells to pass into or out of the tubing. This is a means by which cells can be seeded within the device and/or virus can be delivered to infect cells. In another example, pores can be formed in the membranes themselves to provide a means of perfusing the stacked membranes normal to their surfaces. In this arrangement the flow induces minimal shear forces on cells because the direction of flow is not parallel to the cells; nutrients then reach the cells through diffusion away from these pores.

When seeding cells, both sides of the membranes can be equally seeded. This can be achieved by orienting the membranes and flow parallel to the gravitational field. Since cells naturally settle in media, a perfusion of media equal in magnitude but opposite in direction to the settling velocity can be applied so that the net velocity of the cells with respect to the membranes is close to zero. By symmetry, the cells are equally likely to adhere to either side of the membranes resulting in uniform seeding.

In terms of membrane materials, those with high gas transmission properties are most suitable. This can be accomplished by using materials with high gas permeation (a function of solubility and diffusion rate) such as silicones, including polydimethylsiloxane (PDMS).

Alternatively, it can be accomplished by using very thin membranes because gas transmission rates are generally inversely proportional to membrane thickness. At very thin dimensions, the permeability of the material may also increase significantly, such as is observed with thin parylene (<10 μm). Using this fact, polymers that are conventionally thought of as barriers to gases can become suitably transmissive. Porous membrane materials may also be used since the blow point of small pores can be sufficiently high to allow pressure driven from with the hollow membrane without causing bubbling of gas through the surface. A combination of approaches can also be used to accomplish the desired high gas transmission properties of the membranes.

Surface treatment of the bags can achieve cell adhesion and proliferation. A broadly applicable approach is to coat the membrane with a thin layer of parylene and plasma etch it, using an oxygen plasma treatment and/or an ammonia plasma treatment, to make it hydrophilic.

Additional methods include coating with proteins (e.g. agarose, collagen, fibronectin, fibrin) or other coatings (e.g., lactic acid, laminin, poly-D-lysine, or poly-L-lysine).

TERMS

A "gas permeable" or "semipermeable" material includes that which allows a gas to permeate through but prevent liquid water from permeating, or as otherwise applicable and known in the art. Permeability can be measured at standard room temperature (i.e., 25° C.) and atmospheric pressure or other applicable temperatures and pressures. For example a standard temperature for cultures of mammalian cells is 37° C. For thermophiles, temperatures can go up to 122° C. Pressures can be elevated from or less than standard atmospheric pressure, such as with hydrostatic pressure from being submerged. A gas may be molecular oxygen, carbon dioxide, carbon monoxide, common air, or as otherwise applicable.

A "pillar" or "micropillar" includes a column or other structure that extends perpendicularly from a surface, or as otherwise known in the art. A "micropillar" includes a pillar that is small and is not limited to pillars that are on the scale of micrometers (microns) or micro-inches.

An "array of spacers" includes a geometrically regular or irregular pattern of micropillars or other spacers with a height and center-to-center spacing of the spacers configured to keep the sheets at a fixed distance from one another, or as otherwise known in the art.

A "collapse resistant bag" includes a bag that has spacers inside it such that internal surfaces of opposite sides are prevented from touching each other in normal operation.

An "expansion resistant bag" includes a bag that has internal weld points, connected spacers, or other connections that prevent the bag from becoming shaped like a balloon when pressurized, or as otherwise known in the art. An expansion resistant bag may lay substantially flat. It may have convex and concave recesses and curves.

"Hermetically sealed" simply means sealed to be airtight, or at least not permeable to liquid but perhaps permeable to gas, or as otherwise known in the art.

Open cell foam that may be compatible with certain embodiments includes Atlantic Gasket Corp. Style AG1300-S or AG1300-SM open cell silicone foam, with skin in accordance with ASTM D3183, and McMaster-Carr silicone foam sheets.

Figure 1B:
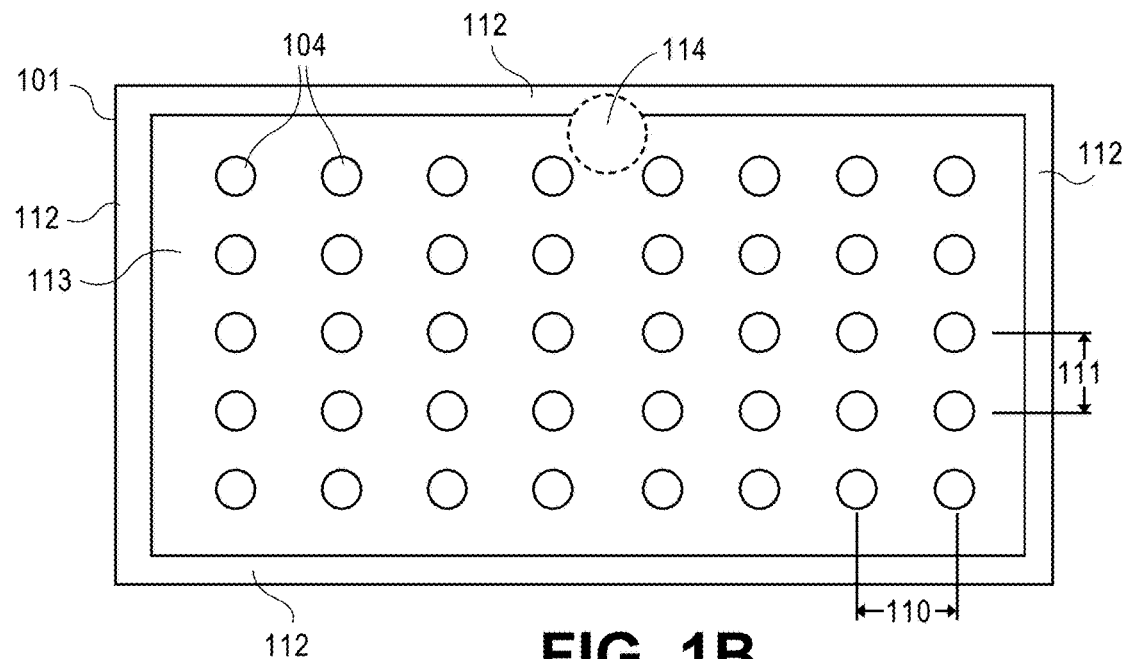
FIG. 1B illustrates cross section B-B of FIG. 1A.

FIGS. 1A-1B illustrate a gas permeable, expansion resistant, collapse resistant bag in accordance with an embodiment. System 100 includes a pair of gas permeable, PDMS polymer sheets 102 and 103. The sheets' perimeters have been hermetically sealed around their edges to form expansion resistant bag 101 with interior cavity 113.

Bottom sheet 103 has integrally formed edge 112 around its perimeter and spacers, which are microfabricated pillars 104, along one face. Micropillars 104 are in a geometrically regular array of columns and rows. Each column of micropillars is separated by distance 110, and each row of micropillars is separated by distance 111. In some embodiments, the distances are different; in others, the distances are the same.

Other configurations are envisioned, including geometrically regular arrays with staggered rows or columns, circular arcs of pillars, sub shapes, and other patterns, as well as geometrically irregular arrays, such as randomly distributed speckles of pillars.

During fabrication, sheet 102 or the tops of the micropillars and edge of sheet 103 were coated with uncured polymer, and then sheet 102 is placed atop sheet 103 before curing. The sheets 102 and 103 and middle portion 112 form a collapse resistant sandwich of layers.

On the outside of sheets 102 and 103 is parylene biocompatible coating 115. The biocompatible coating has a thickness between 0.01 µm and 1000 µm, which may control the gas permeability of the underlying sheet. That is, the PDMS may be permeable to liquids at its nominal thickness; however, the thin coating of parylene prevents liquids from going through them but allowing gas, thus rendering the sheets gas permeable.

Surface treatment 116 covers a portion of biocompatible coating 115. The parylene was subject to an oxygen plasma treatment and ammonia plasma treatment in order to improve cell adhesion.

Figure 1C:
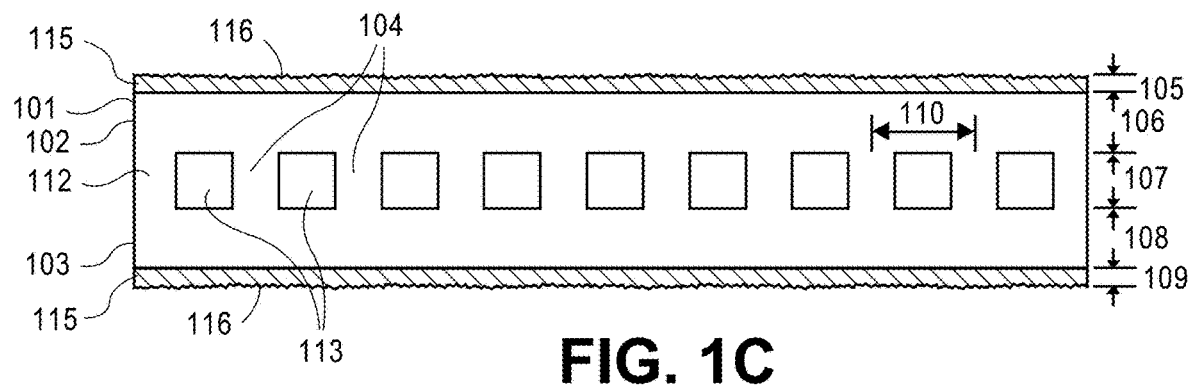
FIG. 1C illustrates cross section C-C of FIG. 1A.

In FIG. 1C, going from top to bottom, top biocompatible coating 115 has thickness 105, sheet 102 has thickness 106, micropillars 104 have equal heights 107, sheet 103 has thickness 108, and bottom biocompatible coating 115 has thickness 109. The thickness of the biocompatible coating, if it is parylene N, parylene C, parylene D, or parylene AF-4, is between 2 µm and 10 µm, preferably between 5 µm and 6 µm.

Height 107 of micropillar spacers 104 is more than one fifth the center-to-center spacing of the micropillar connection points. This height prevents opposing sheets 102 and 103 from bending inward and clinging to each other within the internal cavity, helping to make the bag collapse resistant.

Inlet 114 is formed as a hole through top sheet 102 and biocompatible layer 115. Inlet 114 may be used for supplying gas, or removing gas, from bag 101.

Figure 2A:
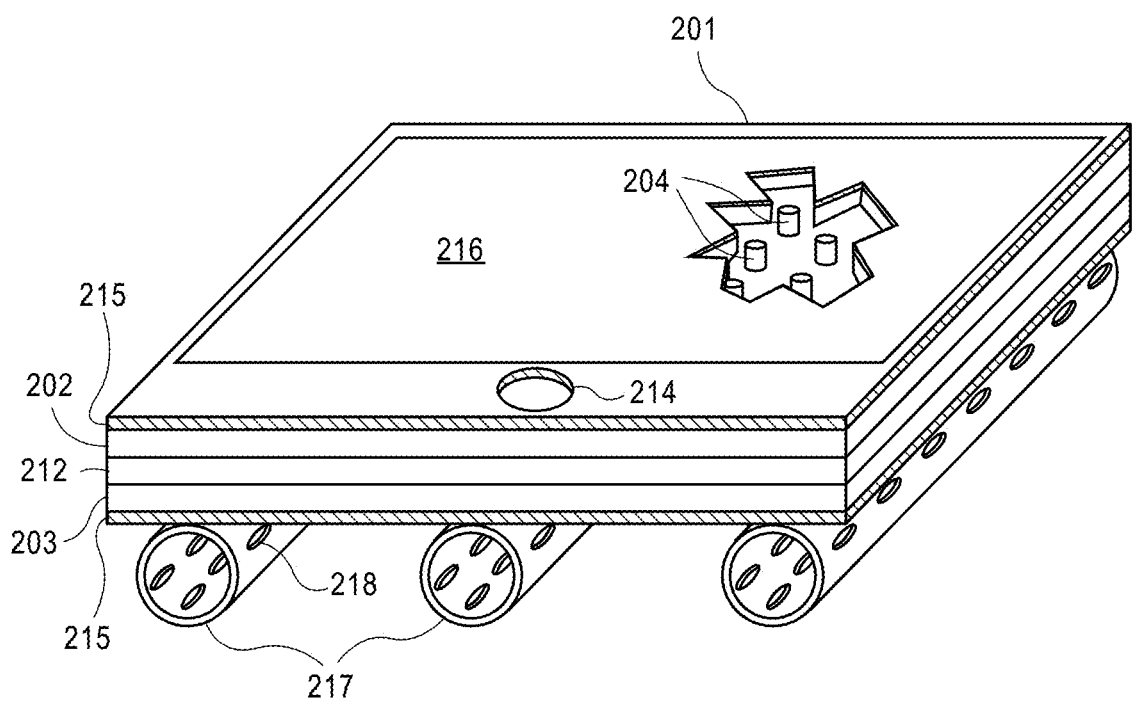
FIG. 2A is an isometric view of a gas-permeable bag with spacer tubes in accordance with an embodiment.
Figure 2B:
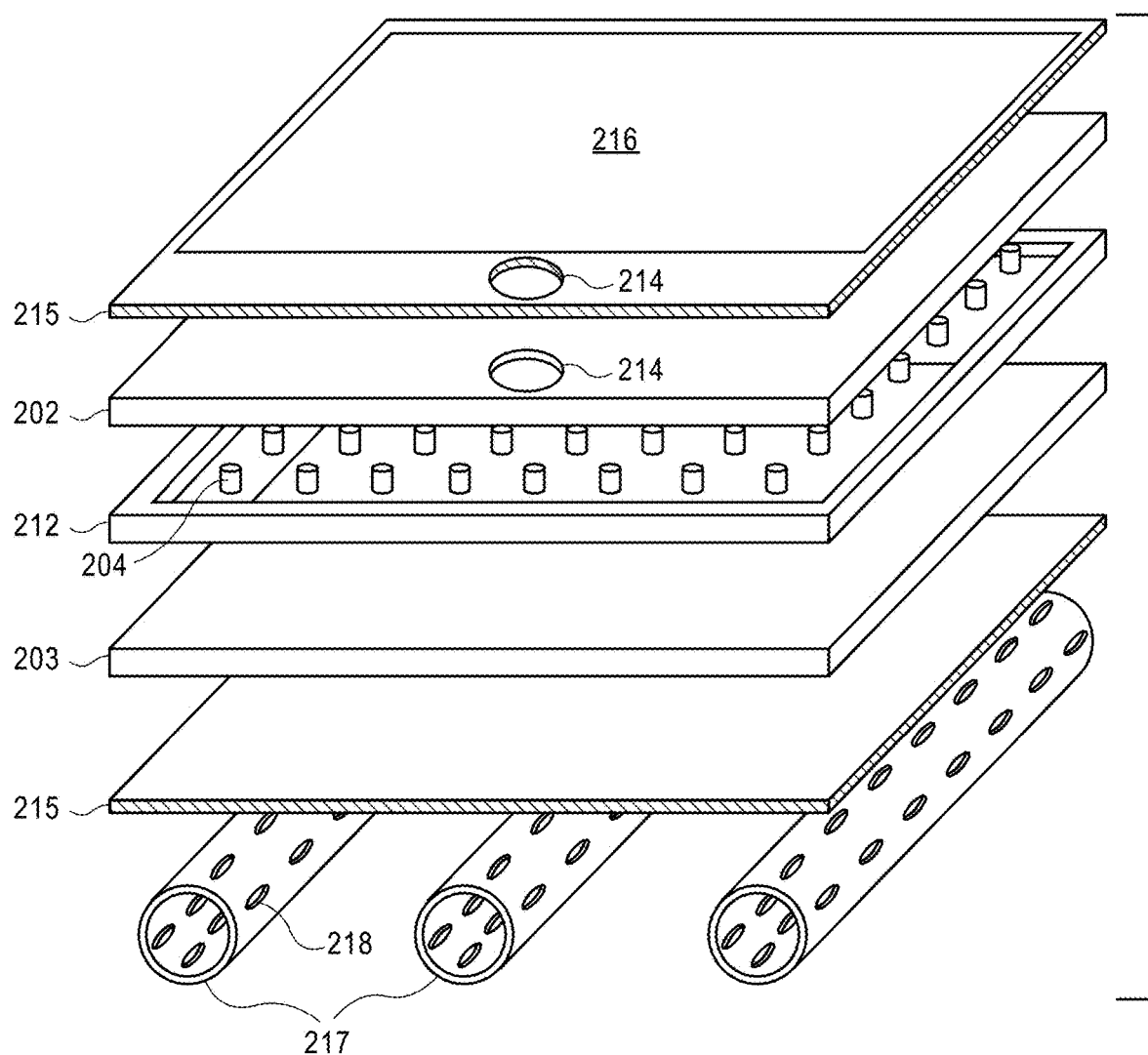
FIG. 2B is an exploded view of the gas-permeable bag of FIG. 2A.

FIGS. 2A-2B illustrate a gas-permeable bag with spacer tubes in accordance with an embodiment. Bag 201 includes biocompatible layers 215 over sheets 202 and 203 with middle layer 212. Inlet 214 is formed in sheet 202 and its biocompatible layer 215, with surface treatment 216 shown on biocompatible layer 215. Also shown is a cutaway view to inside the bag where micropillars 204 keep the bag from collapsing.

Below bag 201 are external spacer tubes 217. Each spacer tube 217 has multiple holes 218 that allow fluid, nutrients, seed cells, and other material to flow out of them. The spacer tubes resemble a French drain or garden soaker hose. However, the spacer tubes are microfabricated, allowing cell-sized or smaller materials to be distributed relatively evenly. Thus, if bag 201 were stacked with other bags and separated by spacer tubes, the spacer tubes could be used to evenly seed cells, spread nutrients, and accumulate discharged waste.

FIGS. 3A-3B illustrate a gas permeable microfabricated array-welded bag. In system 300, bag 301 includes sheets and no additively formed inner pillars to keep apart the sheets. Instead, the sheets are kept apart by mild gas pressure inside of the bag.

An array of connection points 319 was created by pressing a heated iron against the sheets with a heat-insulative mask therebetween, such that the only areas that are welded are those exposed by through holes in the mask. The areas around the welds allow air to move freely. This slightly resembles an inflatable swimming pool air mattress. However, the connection points of the embodiment are less-than-or-equal-to (≤) 2000 µm apart from one another. In some embodiments, the center-to-center spacing of the connection point welds are between 100 µm and 1000 µm. Such tiny spacings can be formed using microfabrication techniques, such as photolithography. Further, the polymer sheets are less than 200 µm thick in the exemplary embodiment.

Perimeter edge 312 is hermetically sealed to form bag 301, and hole 314 is formed in at least one of the sheets; here, hole 314 is formed in sheet 302. Biocompatible layers 315 are on the outside of sheets 302 and 303.

When provided oxygen through inlet hole 314, interior portion 313 opens up and expands. If the pressure of provided air is great enough, even a submerged bag's dry interior portions 313 open up so that the gas can flow freely to the farthest reaches of the bag. The oxygen then evenly permeates through sheets 302 and 303, through biocompatible layers 315, to consuming cells outside.

FIG. 4 illustrates an open-cell foam gas permeable bag. In system 400, a 0.1 mm to 1.5 mm thick mat of polymeric open-cell foam 421 has gas permeable skin sheets 420 on opposing sides. That is, naturally formed skins on opposing sides of the foam are permeable to gas. The foam's perimeter edge 412 (shown exploded away from the central foam area in the figure) is hermetically sealed so as to bond skin sheets 420 together and enclose the open-cell foam in an interior cavity. The foam prevents the bag from expansion and collapse. Thus, an expansion-resistant, collapse-resistant bag is formed.

Biocompatible coating 415 is layered over the outside skins 420 of the bag, and it has a thickness of 0.01 µm to 1000 µm.

Figure 5:
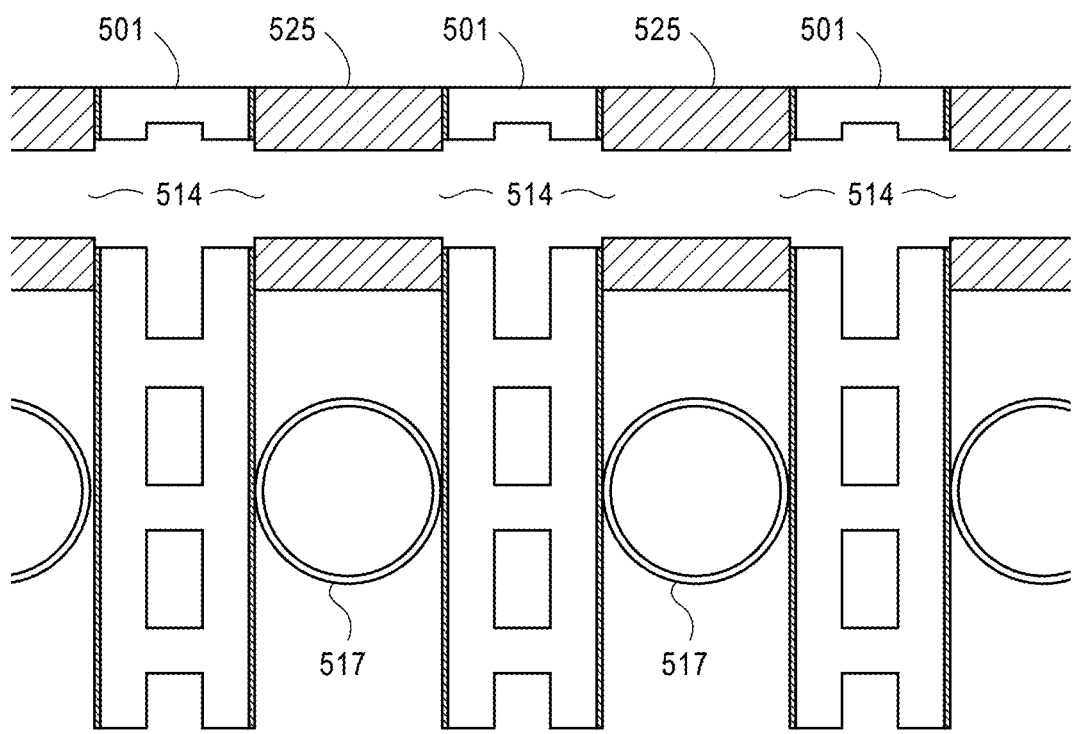
FIG. 5 illustrates multiple bags separated by spacer tubes in accordance with an embodiment.

FIG. 5 illustrates multiple bags separated by spacer tubes. Each bag 501 is shown in cross section, and each bag has hole 514 through both sheets. O-rings 525, shown in cross-section, space apart the bags at a predetermined distance and seal the insides of the bags to one another. Air or oxygen may be supplied through the o-rings so that the gas flows into each of the bags.

Besides the o-rings, also spacing apart bags 501 are tube spacers 517, which are shown in cross section. Tube spacers 517 may have holes, slits, or other portions through which nutrients, seed cells, or other materials may be sent to be evenly distributed.

In some embodiments, tube spacers 517 may be oriented so that they extend up and down as opposed to how they are shown (i.e., in and out of the page). In other embodiments, tube spacers may snake around between the bags.

Figure 6:
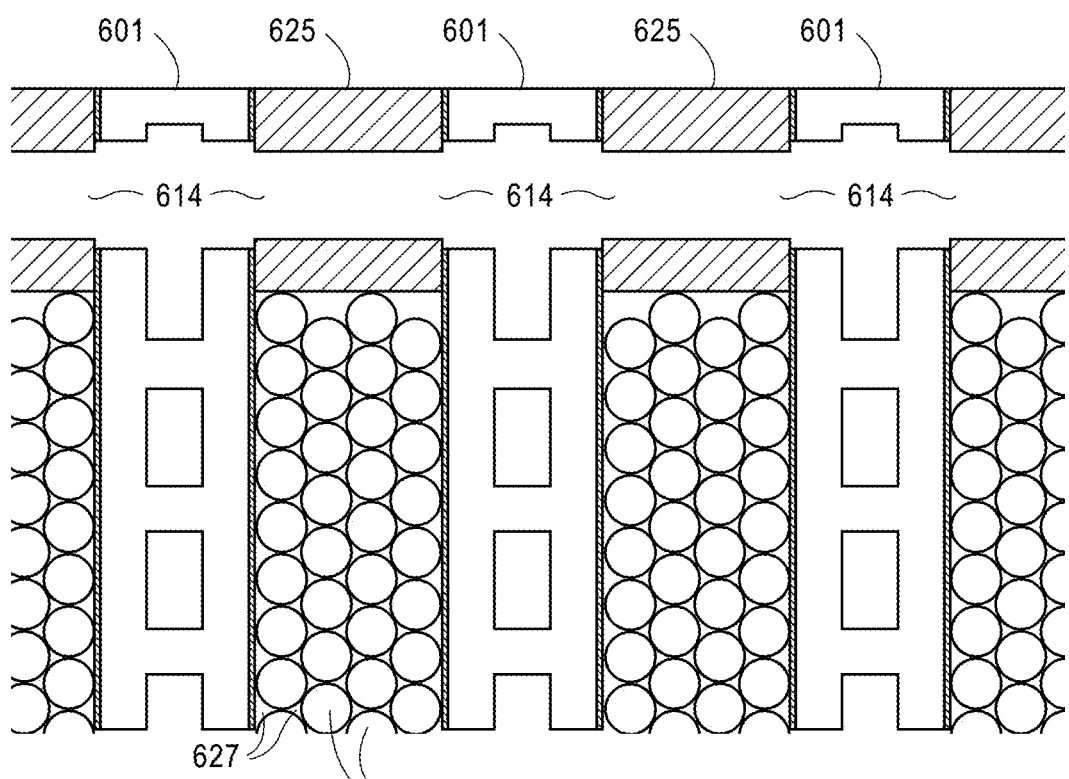
FIG. 6 illustrates multiple bags separated by beads in accordance with an embodiment.

FIG. 6 illustrates multiple bags separated by beads. Each bag 601 is shown in cross section, and each bag has hole 614 through both sheets. O-rings 625, shown in cross-section, space apart the bags at a predetermined distance and seal the insides of the bags to one another Bags 601 are kept separated by spherical beads 626. The beads provide more surface area for cell growth than just the bags. Cells may be seeded within interstitial spaces 627 between the beads and the bags, and a liquid culture of nutrients can be flowed therethrough. The beads' outsides may be treated for better cell adhesion, to hold nutrients, etc. Meanwhile, gas is provided into the dry interiors of the bags through the o-ring manifold.

After the cells have grown, the bags may be removed from the beads by pulling the bags out or draining the beads from in between the bags. The beads may then be processed to remove the cells from them. For example, trypsin may be added to cleave the bonds between the cells and the beads (and bags), or the beads may be vigorously washed so that the cells come off.

Figure 7:
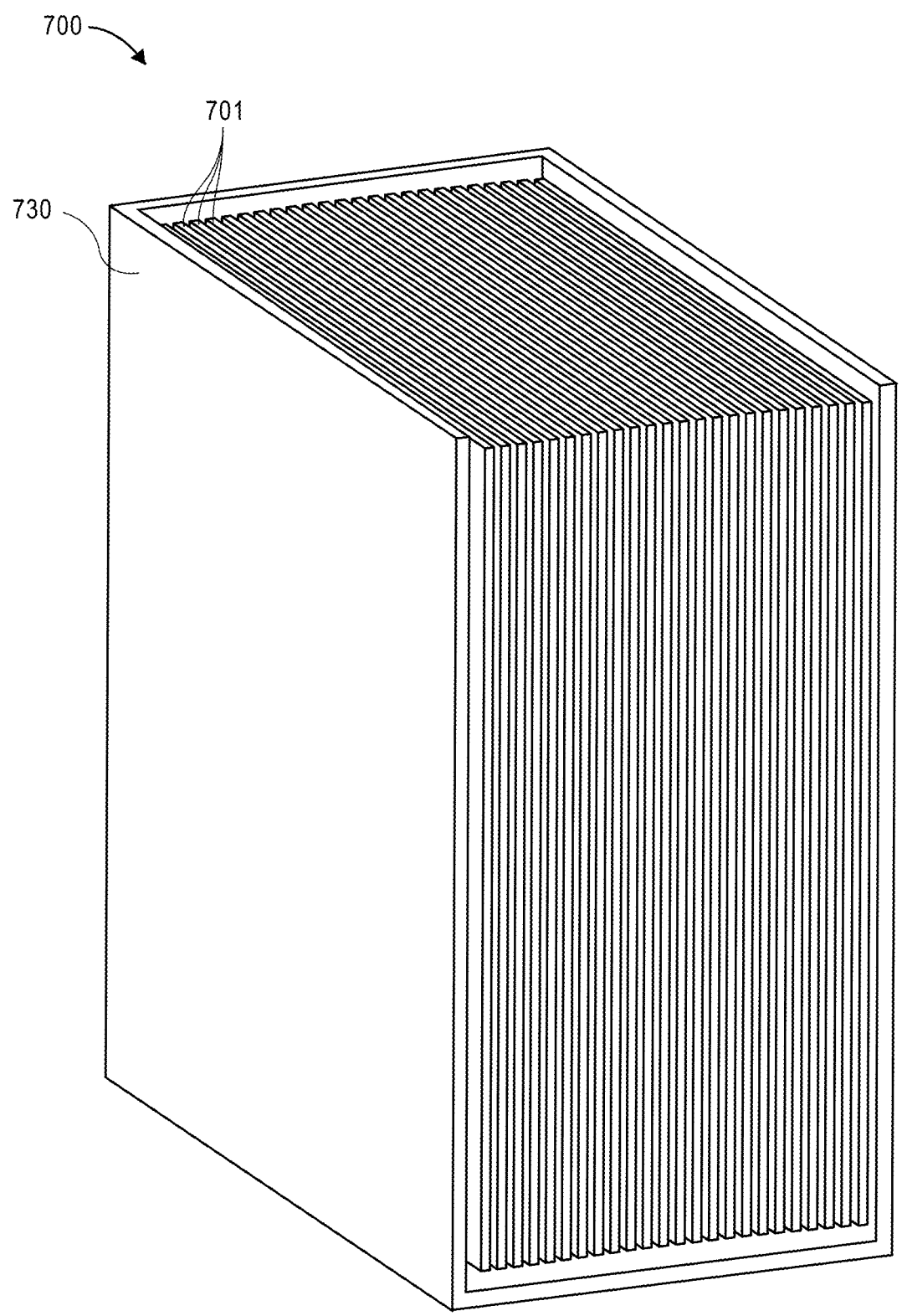
FIG. 7 is an isometric view of a bioreactor vessel having stacked gas permeable bags in accordance with an embodiment.

FIG. 7 is an isometric view of a bioreactor vessel having stacked gas permeable bags. In system 700, bags 701 are spaced apart by a predetermined amount, and they are hung in vertical planes so that their walls are vertical with respect to gravity. In other configurations, a long bag may be coiled around itself, like a paper towel roll.

Watertight vessel 730 contains the bags and immerses them in a liquid culture. The liquid may be circulated gently while a manifold delivers oxygen or air to the bags. Openings to the bags may be connected to one another, such as in FIGS. 5-6, or tubes with lumens connecting to the insides of the bags may be connected with a common manifold.

Figure 8:
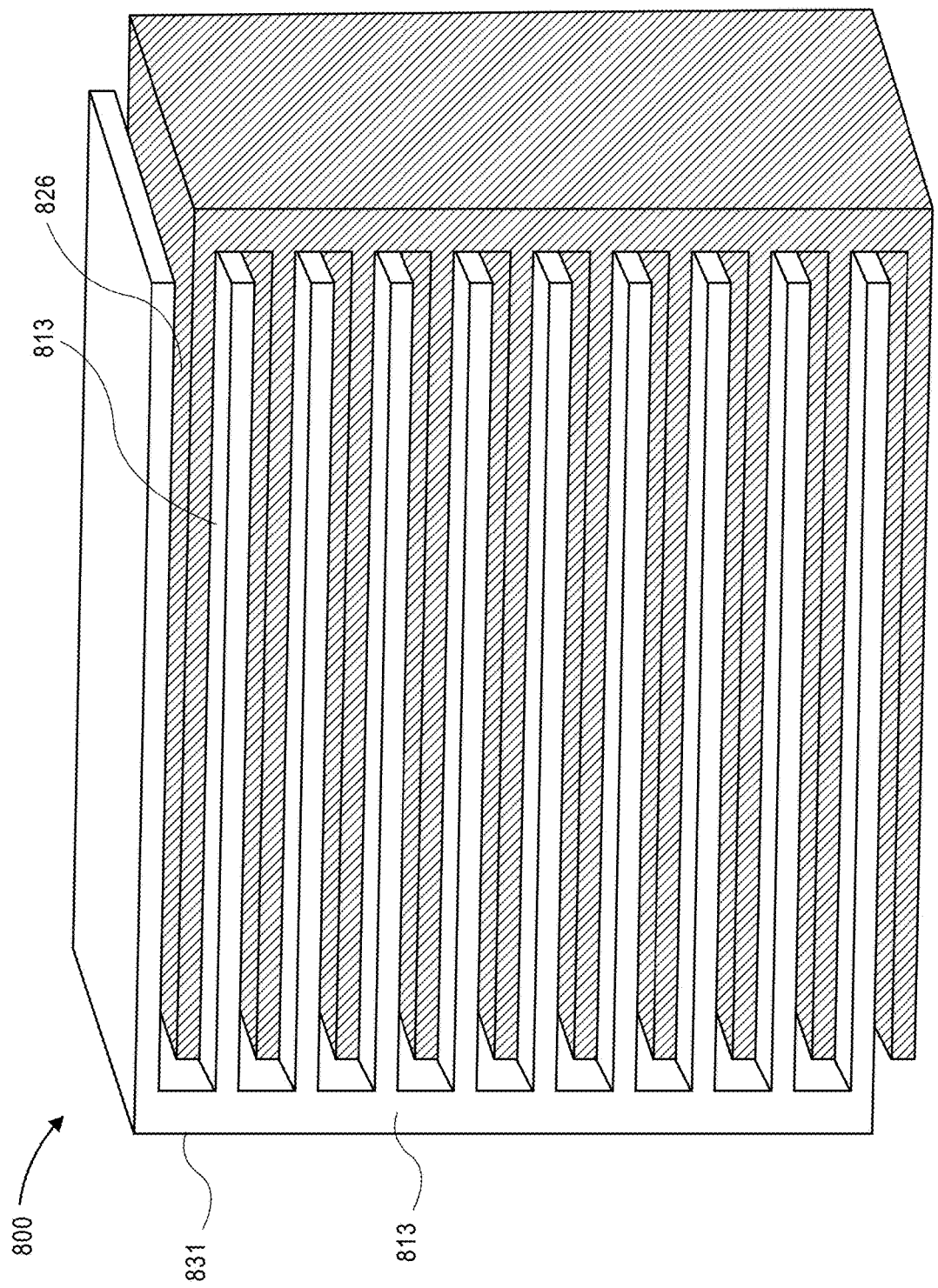
FIG. 8 is an isometric view of a bioreactor with interdigitated nutrient and gas delivery bags in accordance with an embodiment.

FIG. 8 is an isometric view of a bioreactor with inter-digitated nutrient and gas delivery bags. In system 800, structure 831 of gas bag membranes 813 is interleaved with nutrient delivery membranes 826. This forms an extremely compact structure where gas and nutrients are provided throughout the bioreactor.

The bioreactor may be contained in a vessel (not shown in the figure) to contain liquid and cell nutrients.

FIGS. 9A-9F illustrate a microfabricated bag manufacturing process. In FIG. 9A, a continuous dry film mold with elevated edges is set atop a flat silicon substrate. In FIG. 9B, the dry film mold is photolithographically etched to create through holes in the dry film. In FIG. 9C, PDMS is applied over the mold and allowed to cure. The result is a PDMS sheet with micropillars and a tall edge around its perimeter.

In FIG. 9D, PDMS is applied over a mold similar to that in FIG. 9A and allowed to cure. The result is a flat sheet of PDMS. The two sheet of PDMS are then brought together, pillar side of the first sheet between them, and glued using a thin PDMS layer that then cures to create a bag. The micropillars prevent expansion and prevent collapse of the microfabricated bag.

In FIG. 9E, a tube is inserted in a side of the bag so that a lumen of the tube connects through a hole in the hermetically sealed edge of the bag with an interior cavity of the bag. In FIG. 9F, parylene is coated, using chemical vapor deposition (CVD), over top, bottom, and side of the bag. The parylene presents a clean, biocompatible surface for cells. The parylene also controls the permeability of the sheets. The parylene can be plasma treated for better cell adhesion properties.

Figure 10A:
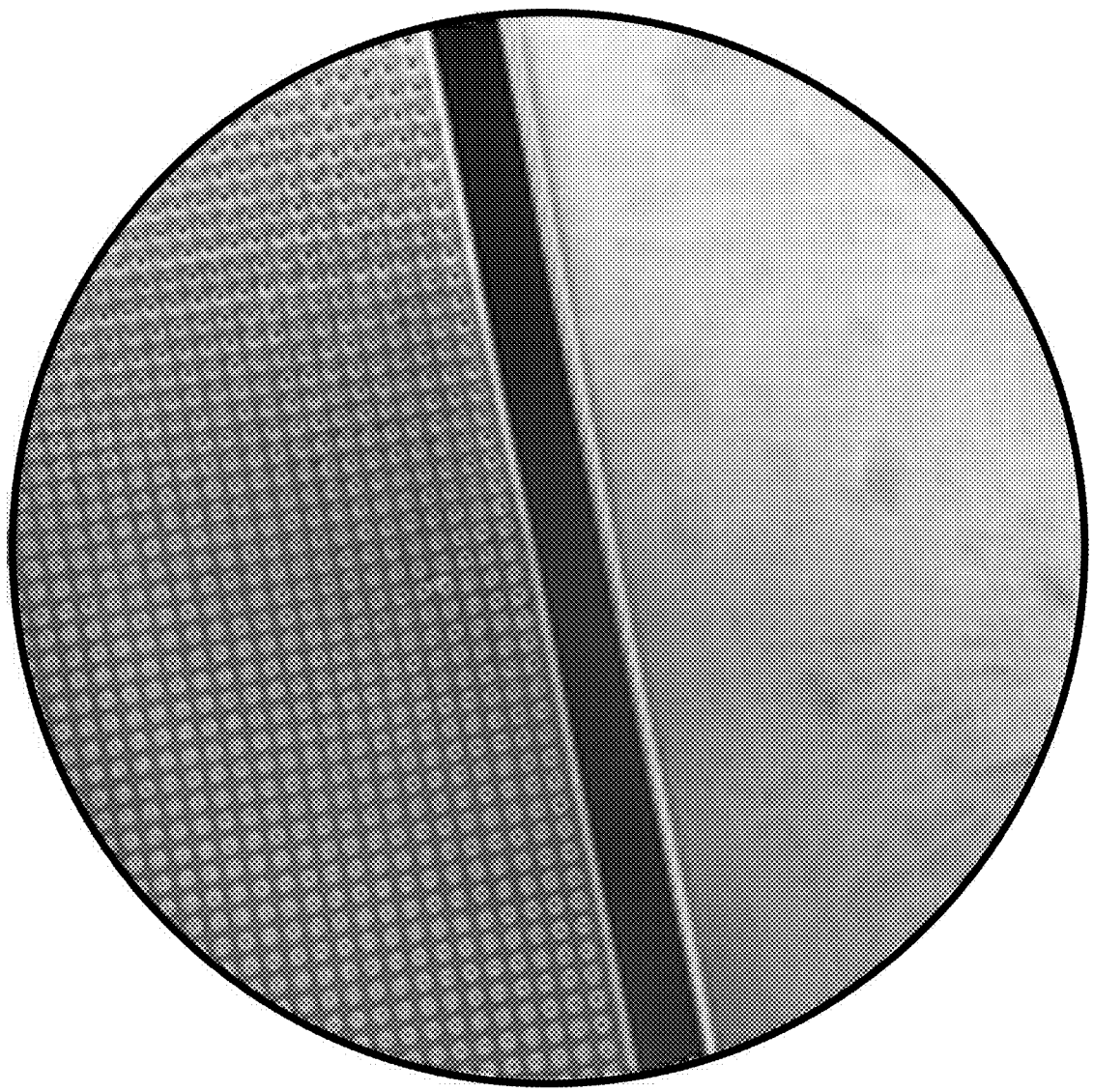
FIG. 10A is a photograph of a prototype expansion resistant, collapse resistant bag in accordance with an embodiment.
Figure 10B:
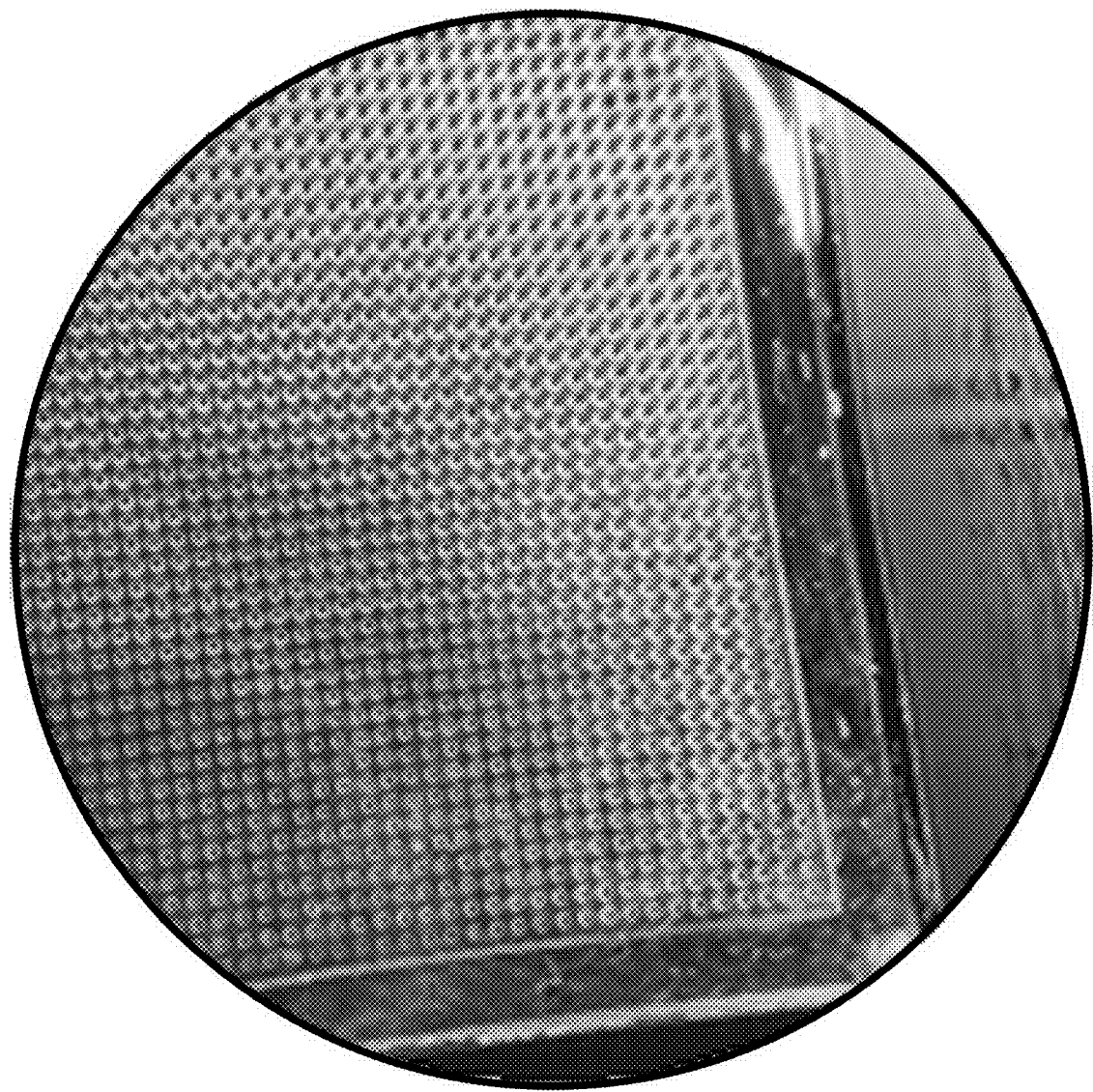
FIG. 10B is a photograph of a corner of the prototype expansion resistant, collapse resistant bag of FIG. 10A.

FIGS. 10A-10B are microscope photographs of a proto-type expansion resistant, collapse resistant bag. The bag is clear so that one may see through to its micropillars within its interior. Evident in the figures is a geometrically regular pattern, columns and rows, of micropillars within the bag. The rows and columns are around 100 µm apart Also shown are the bag's sealed edges, which show up dark in the micrograph.

The hollow PDMS bags/membranes (120 µm thick membranes with a 120 µm central gap) are coated with a thin layer (~0.5 µm) of plasma treated parylene C for cell adhesion. The edges of the bags are plumbed with tubing and connected to a regulated oxygen supply to perfuse the hollow portion of the bag with oxygen. Oxygen within this gap is able to diffuse through the PDMS membrane out into the surrounding media to nourish cells. Cells can be grown directly on the membranes with rates comparable to tissue culture flasks.

Figure 11:
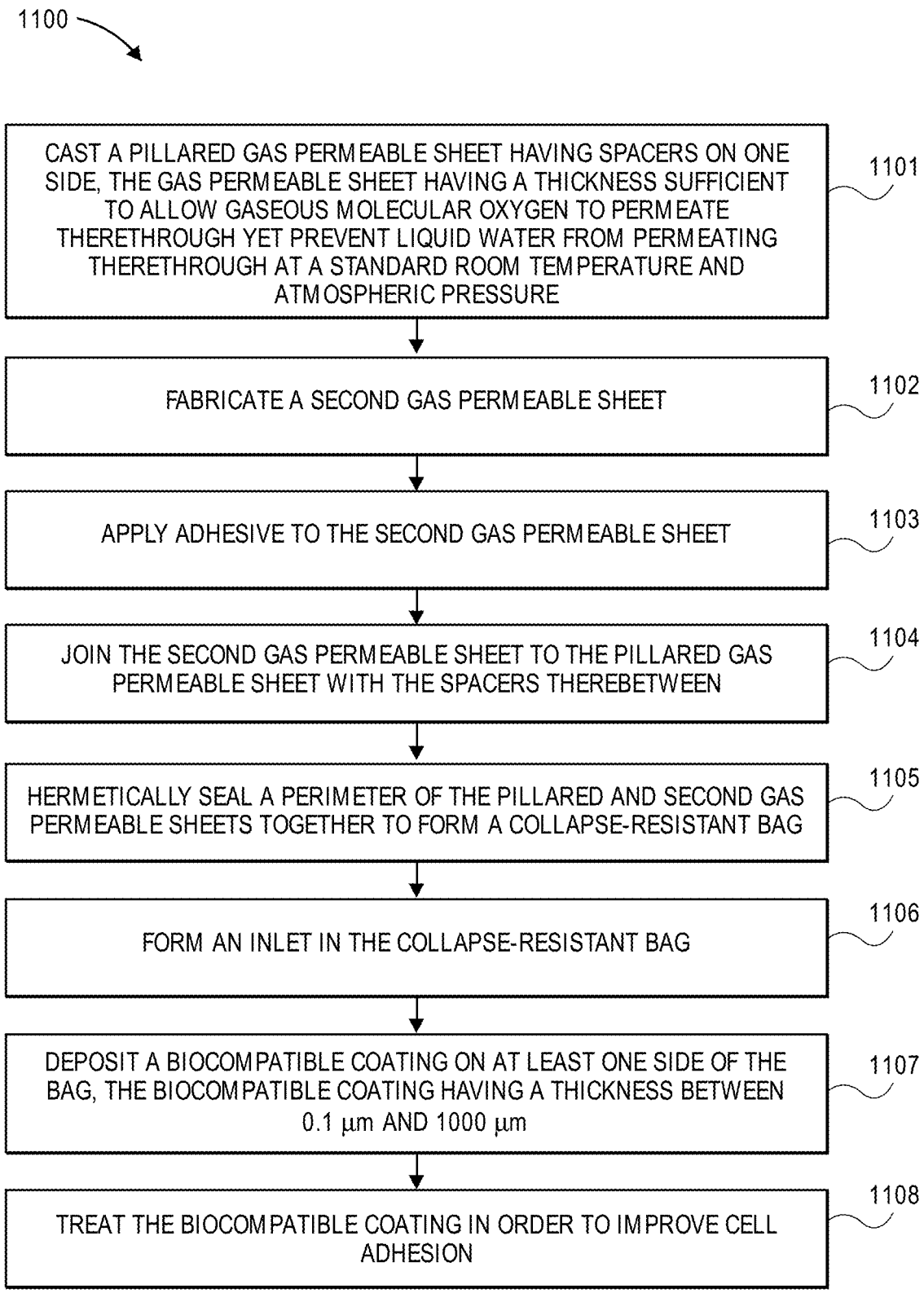
FIG. 11 is a flowchart of a process in accordance with an embodiment.

FIG. 11 is a flowchart of process 1100 in accordance with an embodiment. In operation 1101, a pillared gas permeable sheet is cast with spacers on one side. The gas permeable sheet has a thickness sufficient to allow gaseous molecular oxygen to permeate therethrough yet prevent liquid water from permeating therethrough at standard room temperature and atmospheric pressure. In operation 1102, a second gas permeable sheet is fabricated. In operation 1103, an adhesive is applied to the second gas permeable sheet. In operation 1104, the second gas permeable sheet is joined to the pillared gas permeable sheet with the spacers therebetween. In operation 1105, a perimeter of the pillared and second gas permeable sheets is hermetically sealed together to form a collapse-resistant bag. In operation 1106, an inlet in the collapse-resistant bag is formed. In operation 1107, a bio-compatible coating is deposited on at least one side of the bag, the biocompatible coating having a thickness between 0.1 µm and 1000 µm. In operation 1108, the biocompatible coating is treated in order to improve cell adhesion.

Figure 12:
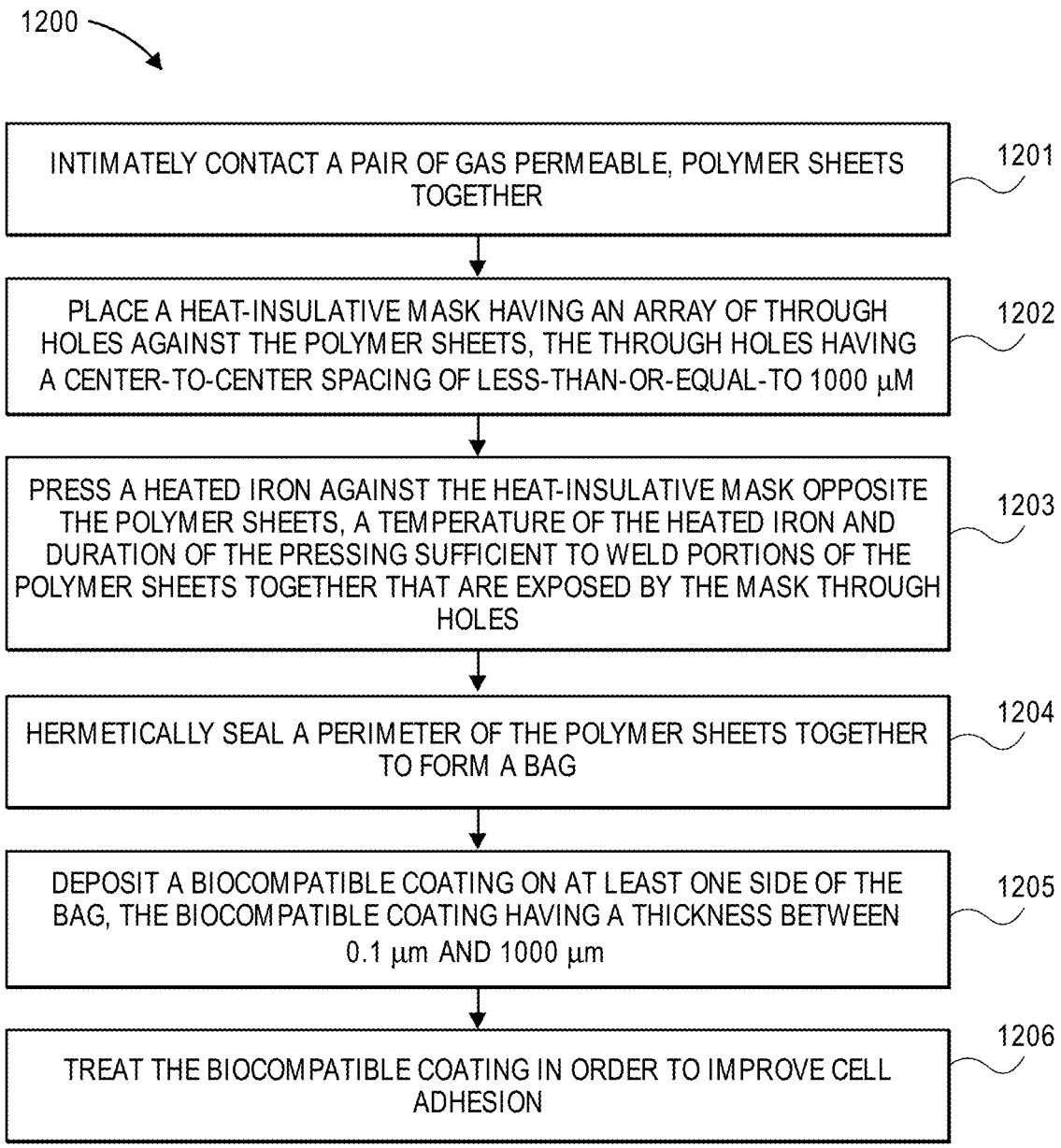
FIG. 12 is a flowchart of a process in accordance with an embodiment.

FIG. 12 is a flowchart of process 1200 in accordance with an embodiment. In operation 1201, a pair of gas permeable, polymer sheets are intimately contacted together. In operation 1202, a heat-insulative mask having an array of through holes is placed against the polymer sheets (on one side), the through holes having a center-to-center spacing of less-than-or-equal-to 1000 µm. In operation 1203, a heated iron is pressed against the heat-insulative mask opposite the polymer sheets, a temperature of the heated iron and duration of the pressing sufficient to weld portions of the polymer sheets together that are exposed by the mask through holes. In operation 1204, a perimeter of the polymer sheets are hermitically sealed together to form a bag. In operation 1205, a biocompatible coating is deposited on at least one side of the bag, the biocompatible coating having a thickness between 0.1 μm and 1000 μm. In operation 1206, the biocompatible coating is treated in order to improve cell adhesion.

Figure 13:
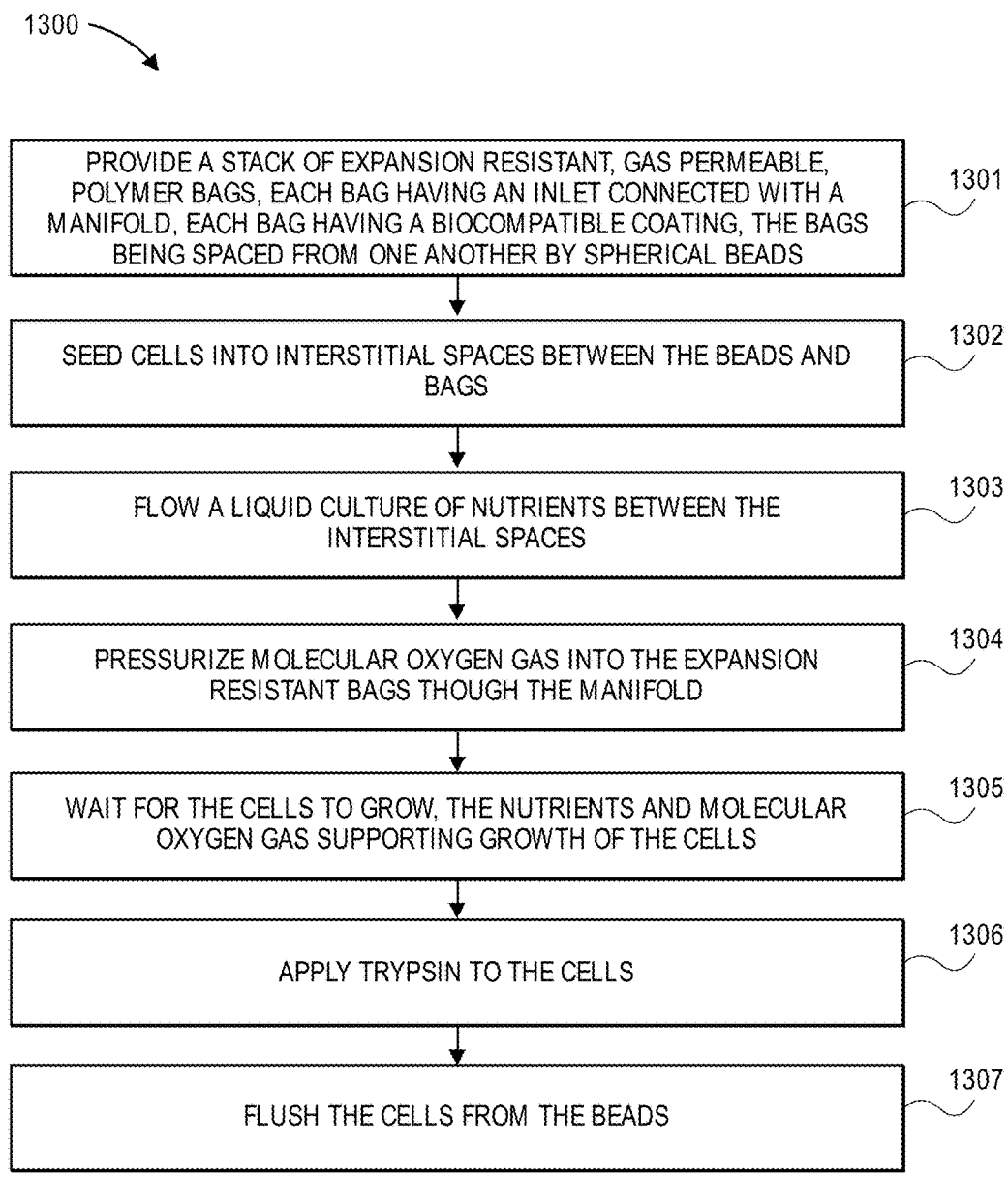
FIG. 13 is a flowchart of a process in accordance with an embodiment.

FIG. 13 is a flowchart of process 1300 in accordance with an embodiment. In operation 1301, a stack of expansion resistant, gas permeable polymer bags is provided, each bag having an inlet connected with a manifold, each bag having a biocompatible coating, the bags being spaced from one another by spherical beads. In operation 1302, cells are seeded into interstitial spaced between the beads and bags. In operation 1303, a liquid culture of nutrients is flowed between the interstitial spaces. In operation 1304, molecular oxygen gas is pressurized into the expansion resistant bags through the manifold. In operation 1305, one waits for the cells to grow and multiply, the nutrients and molecular oxygen gas supporting growth of the cells. In operation 1306, trypsin is applied to the cells. In operation 1307, the cells are flushed from the beads.

The invention has been described with reference to various specific and illustrative embodiments. However, it should be understood that many variations and modifications may be made while remaining within the spirit and scope of the following claims.

What is claimed is:

1. A compact cell-growing apparatus comprising:
   a watertight vessel;
   a stack of biocompatible material-coated, flat, expansion resistant gas permeable bags within the vessel, each bag having an associated inlet to an interior cavity of the bag; and
   spacers between the expansion resistant gas permeable bags,
   wherein each bag comprises:
     a pair of gas permeable, polymer sheets;
     an array of connection points between faces of the polymer sheets;
     a hermetically sealed edge that bonds a perimeter of the sheets together, enclosing the connection points in an interior cavity between the sheets to form an expansion resistant bag; and
     an inlet to the bag fluidly connected with the interior cavity.

2. The apparatus of claim 1 wherein the gas permeable bags are stacked in vertical planes.

3. The apparatus of claim 1 wherein the stack includes at least one gas permeable bag folded over onto itself.

4. The apparatus of claim 1 wherein the stack includes at least one gas permeable bag coiled around itself.

5. The apparatus of claim 1 further comprising:
   o-rings spacing each bag apart and sealing the inlets of the bags to each other.

6. The apparatus of claim 1 wherein each bag comprises:
   the connection points have a center-to-center spacing less-than-or-equal-to 2000 μm.

7. The apparatus of claim 1 wherein each bag further comprises:
   a biocompatible coating over at least one side of the gas permeable sheets, the biocompatible coating having a thickness between 0.01 μm and 1000 μm.

8. The apparatus of claim 6 wherein the center-to-center spacing of the connection points is between 100 μm and 1000 μm.

9. The apparatus of claim 1 wherein each bag further comprises:
   an array of spacers connecting the sheets at the connection points, the spacers having a height sufficient to make the expansion resistant bag collapse resistant.

10. The apparatus of claim 9 wherein a height of the spacers is equal-to-or-greater-than one fifth the center-to-center spacing of the connection points.

\* \* \* \* \*